(12) United States Patent
Allred et al.

(10) Patent No.: US 7,052,275 B2
(45) Date of Patent: *May 30, 2006

(54) KITS AND METHODS FOR BLEACHING AND DESENSITIZING TEETH

(75) Inventors: Peter M. Allred, Riverton, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/646,443

(22) Filed: Aug. 22, 2003

(65) Prior Publication Data

US 2004/0241618 A1 Dec. 2, 2004

Related U.S. Application Data

(63) Continuation-in-part of application No. 10/637,237, filed on Aug. 8, 2003, which is a continuation-in-part of application No. 10/446,235, filed on May 27, 2003, which is a continuation-in-part of application No. 10/446,471, filed on May 27, 2003.

(51) Int. Cl.
*A61C 15/00* (2006.01)
*A61K 9/20* (2006.01)

(52) U.S. Cl. .................. 433/216; 424/53; 433/215

(58) Field of Classification Search .............. 433/80, 433/215, 216; 424/53; 206/63.5, 369
See application file for complete search history.

(56) References Cited

U.S. PATENT DOCUMENTS

| 165,584 | A | 7/1875 | Hopfen |
| 1,637,153 | A | 7/1927 | Lawton |
| 2,257,709 | A | 9/1941 | Anderson .................. 128/260 |
| 2,835,628 | A | 5/1958 | Saffir .......................... 167/84 |
| 3,339,547 | A | 9/1967 | Drabkowski ............... 128/260 |
| 3,527,219 | A | 9/1970 | Greenberg .................. 128/260 |
| 3,577,640 | A | 5/1971 | Lee ............................... 32/32 |
| 3,624,909 | A | 12/1971 | Greenberg ..................... 32/40 |

(Continued)

FOREIGN PATENT DOCUMENTS

| WO | WO 88/06869 | 9/1988 |
| WO | WO 03/000216 | 1/2003 |

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Todd E. Manahan
(74) *Attorney, Agent, or Firm*—Workman Nydegger

(57) ABSTRACT

Kits for bleaching and desensitizing a person's teeth include 1) at least one dental bleaching composition or device in the shape of a dental tray or having a tray-like configuration and 2) at least one dental desensitizing composition or device in the shape of a dental tray or having a tray-like configuration. The shaped treatment compositions comprising the kit have increased adhesiveness to teeth when moistened with saliva or water. The shape of the treatment composition or device facilitates placement of the composition or device over a person's teeth with substantially less manipulation compared to the use of initially flat strips. The substantially solid treatment compositions become more adhesive when moistened with saliva or water, yet remain intact and coherent when protected by a moisture-resistant barrier layer. The substantially solid treatment compositions adhere and remain in place more reliably than treatment strips that include a treatment composition initially in a gel-like condition.

51 Claims, 7 Drawing Sheets

U.S. PATENT DOCUMENTS

| | | | |
|---|---|---|---|
| 3,688,406 A | 9/1972 | Porter et al. | 32/40 R |
| 3,955,281 A | 5/1976 | Weitzman | 32/14 B |
| 4,044,762 A | 8/1977 | Jacobs | 128/136 |
| 4,063,552 A | 12/1977 | Going et al. | 128/136 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir | |
| 4,902,227 A | 2/1990 | Smith | 433/215 |
| 5,008,093 A | 4/1991 | Merianos | |
| 5,051,476 A | 9/1991 | Uji et al. | 525/186 |
| 5,085,585 A | 2/1992 | Zimble | 433/80 |
| 5,108,742 A | 4/1992 | Merianos | |
| 5,112,225 A | 5/1992 | Diesso | 433/48 |
| 5,183,901 A | 2/1993 | Login et al. | |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 | 4/2002 | Trettenerp | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,649,147 B1 | 11/2003 | Ye et al. | |
| 6,682,721 B1 | 1/2004 | Kim et al. | |
| 6,689,344 B1 | 2/2004 | Chang et al. | |
| 6,730,316 B1 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |
| 2004/0005277 A1* | 1/2004 | Willison et al. | 424/53 |

* cited by examiner

KITS AND METHODS FOR BLEACHING AND DESENSITIZING TEETH

CROSS-REFERENCE TO RELATED APPLICATIONS

This application is a continuation-in-part of U.S. application Ser. No. 10/637,237, filed Aug. 8, 2003, which is a continuation-in-part of copending U.S. application Ser. No. 10/446,235, filed May 27, 2003 and a continuation-in-part of copending U.S. application Ser. No. 10/446,471, filed May 27, 2003. The foregoing applications are incorporated herein in their entirety.

BACKGROUND OF THE INVENTION

1. The Field of the Invention

The present invention is in the field of compositions and devices used to bleach and desensitize a person's teeth. More particularly, the invention relates to substantially solid dental bleaching and desensitizing compositions and treatment devices incorporating such compositions in the shape of a dental tray that become adhesive when moistened (e.g., by saliva on a user's teeth), as well as methods for their use.

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray can be expensive.

Because of the time and cost associated with customized trays, less time consuming and costly alternatives have been developed. Contrary to marketing campaigns, however, many alternatives have substantial disadvantages, primarily in terms of their effectiveness (or ineffectiveness) in actually bleaching teeth. They also have their own unique issues relating to ease of use, comfort and poor taste (bleaching compositions are, after all, placed directly into a person's mouth).

One alternative to customized dental trays are non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental Trays that can be self-customized (e.g., so-called "boil and bite" trays) are somewhat more comfortable and better-fitting compared to non-custom trays but less comfortable than trays that are customized by a dentist.

Another alternative tooth bleaching method involves painting a bleaching composition directly onto the surfaces of a person's teeth to be bleached. An advantage of this procedure is that it eliminates the need to obtain a customized tray, or even a non-custom tray. The main disadvantage, however, is that the bleaching composition remains directly exposed to the person's saliva and disruptive forces and movements normally found within a person's mouth. The result is that a significant portion of the bleaching composition does not remain on the tooth where bleaching is desired. Instead, some or all of the composition can dissolve away into the person's saliva and/or be transferred to adjacent oral tissues. Because paint-on dental bleaching compositions, like all dental bleaching compositions, contain peroxide-based bleaching agents, irritation to soft oral tissues within the user's mouth and throat is a potential problem when using such compositions.

Yet another alternative tooth bleaching method involves placing a flexible bleaching strip over a user's tooth surfaces. Bleaching strips typically comprise a flexible plastic strip coated with a moist dental bleaching gel on the side of the strip facing the user's teeth. To install the bleaching strip, a portion of the bleaching strip is first placed over the front surfaces of the user's teeth, followed by folding the remainder of the strip around the occlusal edges of the teeth and back against a portion of the lingual surfaces. Like paint-on bleaching compositions, this procedure does not require the user to obtain a customized tray, or even a non-custom tray, into which a bleaching composition must be placed by the user prior to use. An advantage of bleaching strips over paint-on bleaching compositions is that bleaching strips include a barrier that, at least in theory, protects the dental bleaching gel from diffusing into the user's mouth.

In reality, however, because of the generally poor adhesion of bleaching strips to the user's teeth, coupled with their generally flimsy nature, it is often difficult for the user to maintain the bleaching strips in their proper position. Bleaching strips are prone to slip off the teeth through even minimal movement of the user's mouth, jaw or tongue. Indeed, it is recommended that the user not eat, drink, smoke or sleep while wearing the bleaching strip. In practice, it is difficult to talk while maintaining the bleaching strips properly oriented over the teeth to be bleached.

Even if a user successfully maintains the bleaching strip in its proper position during the entire bleaching event, the flowable bleaching gel can diffuse into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially exposing a new portion of the bleaching gel that remains adhered to the newly exposed surface of the user's teeth. In some cases, the bleaching strip can become so dislodged or mangled that it must be removed by the user and replaced with a fresh bleaching strip to complete the recommended bleaching time. This multiplies the cost and hassle of the bleaching strip method.

In practical terms, the use of bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are prone to move the least is at night while the person is sleeping. Unfortunately, it is recommended that bleaching strips not be used while sleeping, presumably to prevent accidental choking on an inadvertently dislodged bleaching strip. This only confirms the tendency of such bleaching strips to easily dislodge from a user's teeth.

Ultimately, the main impediment to successful bleaching is the failure of users to complete the prescribed bleaching regimen. If the bleaching apparatus is difficult to use, requires numerous repetitions to achieve observable results, or is simply uncomfortable or a hassle to wear, the user may simply give up and abort the bleaching process altogether. Thus, even if significant dental bleaching is possible using a particular bleaching product, it is less likely to occur where the inadequacies of the bleaching apparatus or method causes users to become discouraged before desired results are attained.

Tooth sensitivity is a common problem for many dental patients and can impede dental bleaching regimens due to patient discomfort and pain. Sensitivity may result from or be associated with the existence of a cavity, tooth or root fractures, gingival recession, exposed dentin, toothbrush abrasion, bleaching, attrition, erosion, grinding, or trauma from periodontal disease. Tooth sensitivity can become so uncomfortable that it may prevent a patient from eating or drinking certain foods, being outdoors in cold weather, or maintaining good oral hygiene practices. Tooth sensitivity is also a common complaint during dental bleaching regimens. Dental bleaching compositions, which typically comprise a peroxide bleaching agent, can cause tooth sensitivity and pain that, if left untreated, may cause the user to prematurely abort the bleaching process.

To relieve tooth sensitivity, there are currently many non-permanent treatment options available. The most common options include using desensitizing toothpastes, varnishes, gels, and rinses. These products may include, but are not limited to, desensitizing agents such as potassium nitrate, other potassium salts, citric acid, citrates, strontium chloride, stannous fluoride, and sodium fluoride.

Desensitizing dentifrices are a popular treatment option in treating sensitivity. To use desensitizing dentifrices, it is usually recommended that the patient use the dentifrice twice daily. However, results are not immediate. It usually takes an extended period of time (about 1–4 weeks) to be effective and to relieve sensitivity. The main reason for this is that people typically only brush their teeth for about 60 seconds or less, which translates into extremely limited contact time between the desensitizing agent and the person's teeth.

An alternative treatment involves the use of desensitizing gels that are applied using custom-fitted or non-customized trays, such as those mentioned above for bleaching teeth.

In view of the foregoing, there is an ongoing need for improved bleaching and desensitizing compositions and devices that are simple and easy to use, that more reliably remain in position over the user's teeth, and that result in less diffusion of bleaching or desensitizing composition into a user's oral cavity. Such improvements would be expected to improve or encourage compliance by the user.

BRIEF SUMMARY OF THE PREFFERED EMBODIMENTS

The present invention generally relates to kits and methods for bleaching and desensitizing teeth. The inventive kits include one or more dental bleaching compositions or devices used to bleach a person's teeth and one or more dental desensitizing compositions or devices used to desensitize a person's teeth. Such compositions or devices are shaped like a dental tray or have a tray-like configuration. The substantially solid dental bleaching and desensitizing compositions become more adhesive to teeth when moistened (e.g., by saliva or water). When placed over a person's teeth, the dental bleaching and desensitizing compositions reliably adhere to the teeth, maintaining contact between the teeth to be treated and the active agent.

In one embodiment, the bleaching and desensitizing compositions (hereinafter, "treatment composition" or "treatment compositions") are used in combination with a barrier layer that protects the treatment composition from ambient saliva or moisture found within the person's mouth. To the extent that a barrier layer is subsequently applied or attached to a shaped bleaching or desensitizing composition, the treatment composition may be considered to be an intermediate to a finished bleaching or desensitizing device comprising the treatment composition (or layer) and the barrier layer.

The optional barrier layer advantageously comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin, polyester, polyurethane, or similar moisture-resistant material. The barrier layer may comprise a conventional dental tray, examples of which include both customized and non-custom dental trays. The barrier layer may be as simple as a layer of a moisture resistant barrier forming material that is sprayed or painted on, applied by dipping, or otherwise applied to an existing bleaching or desensitizing layer (hereinafter, "treatment layer") comprising a substantially solid treatment composition (e.g., one that is in the form of a dental tray or that otherwise has a desired shape).

The inventive treatment compositions are substantially solid and coherent, as opposed to a liquid, gel, paste, or dry particulate or powdery bleaching or desensitizing composition. As such, the treatment compositions comprise one or more coherent regions or masses of a dental bleaching or desensitizing composition that does not readily run or flow. Providing a substantially solid and coherent treatment composition better adheres to a person's teeth and does not readily diffuse into the surrounding oral cavity on its own, absent becoming diluted by saliva or moisture in a person's mouth. This helps maintain the treatment composition between the optional barrier layer and the teeth being treated and helps prevent diffusion of the active agent into the surrounding oral cavity. This, in turn, promotes better tooth bleaching or desensitizing, patient compliance, and reduces the tendency of the user to taste the bleaching or desensitizing composition when in use.

The substantially solid dental treatment compositions according to the invention include at least one dental desensitizing agent and at least one dental bleaching or desensitizing agent as an active dental treatment agent. Preferred dental bleaching agents include solid complexes of hydrogen peroxide (e.g., carbamide peroxide and sodium perborate). A preferred desensitizing agent is potassium nitrate. Non-limiting examples of dental desensitizing agents include other potassium salts, citric acid, citrates, strontium chloride, sodium fluoride, and stannous fluoride.

In one embodiment, the tooth adhesion agent advantageously remains substantially non-adhesive when the dental desensitizing composition is in a dry or substantially solid condition but becomes adhesive to teeth when the dental desensitizing composition is moistened, e.g., with water or saliva. A non-limiting example of a suitable tooth adhesion agent is polyvinyl pyrrolidone (PVP), although it is within the scope of the invention to use other tooth adhesion agents known in the art.

Dental bleaching compositions or layers according to the invention may include a desensitizing agent or other active agent in combination with the dental bleaching agent. Similarly, dental desensitizing compositions or layers according to the invention may include a dental bleaching agent or other active agent in combination with the desensitizing agent. Examples of other components or active agents include, but are not limited to, plasticizers and humectants (e.g., glycerin, sorbitol, and polyethylene glycol), volatile solvents (e.g., water and alcohols), stabilizing agents (e.g., EDTA), neutralizing agents, thickening agents (e.g., fumed silica), remineralizing agents (e.g., sodium fluoride or other fluoride salts), antimicrobial agents (e.g., chlorhexidine), antiplaque agents, anti-tartar agents, other medicaments, flavorants, sweeteners, and the like.

According to one embodiment, dental treatment compositions according to the invention are made by first forming a flowable liquid or gel composition that is subsequently dried to form a substantially solid treatment composition or layer. This may be performed by heating or otherwise causing one or more volatile solvents to be driven off by evaporation, thus leaving behind a substantially solid treatment composition. The drying process may be performed before or after the treatment composition is placed into contact with a barrier layer.

According to one embodiment, shaped treatment compositions according to the invention can be made by spreading a flowable precursor composition onto the surface of a large or continuous polymeric sheet. The polymeric sheet and precursor composition are then heated, such as in a forced air oven, to drive off a substantial portion of the water or other solvent that was used to form the flowable precursor composition in order to yield a substantially solid layer of the treatment composition. Thereafter, individual tray-like dental bleaching or desensitizing devices can be molded or stamped from the large or continuous polymeric sheet coated with the substantially solid layer of bleaching or desensitizing composition and then separated as individual bleaching or desensitizing devices suitable for placement over a person's teeth. Such treatment devices include a treatment layer comprising a shaped dental bleaching or desensitizing composition according to the invention. Alternatively, a solid sheet comprising the treatment composition can be separated from the polymer sheet and molded, stamped or otherwise formed into a desired shape.

Alternatively, a flowable or substantially solid treatment composition can be molded or shaped into a desired tray-like configuration comprising the treatment layer. Alternatively, the flowable precursor composition can be cast onto a forming surface and dried to form a substantially solid sheet of bleaching or desensitizing composition that is thereafter molded, stamped or otherwise formed into a desired shape. Thereafter, a barrier layer can be attached or applied to an outer surface of the treatment layer. In yet another embodiment, a dental tray can be coated with a flowable dental bleaching or desensitizing composition, such as by painting or spreading, and then heated or allowed to dry at room temperature so that the treatment composition becomes substantially solid.

The size and shape of treatment compositions and devices according to the invention can be tailored to more readily fit a person's upper or lower dental arch. They may also be tailored to fit persons having differently sized or shaped dental arches. The dental treatment compositions and devices are advantageously designed so as to substantially cover the front and lingual surfaces of the teeth to be desensitized. Bleaching both surfaces yields more esthetically appealing teeth. Moreover, bleaching both the front and lingual surfaces helps in bleaching the interproximal spaces between adjacent teeth. Similarly, desensitizing both surfaces helps in desensitizing the whole tooth, not just one side. The dental treatment compositions and devices are advantageously flexible and adhesive so as to readily conform to a wide variety of differently-sized teeth and dental arches.

The dental treatment compositions and devices according to the invention are preferably in the shape of a dental tray having a front side wall, a rear side wall, and a trough between the front and rear side walls. Having the shape of a dental tray facilitates placement of the dental treatment composition or device over a person's teeth by minimizing the amount of manipulation that is necessary to obtain a good fit between the composition or device and the person's teeth. Dental treatment devices that are in the shape of a dental tray and that have a substantially solid treatment layer that becomes more adhesive when moistened with water or saliva are easier to install over a person's teeth than flat bleaching strips. In addition, the inventive treatment devices are designed to more reliably remain in place over the person's teeth compared to conventional bleaching strips. The result is more effective bleaching and desensitization and better patient compliance.

According to one embodiment, the dental treatment composition or device has a horseshoe shape and a U-shaped trough like a conventional dental treatment tray. In another embodiment, the treatment composition or device has an L-shaped profile or "trough". It will be appreciated, however, that dental treatment compositions or devices according to the invention can have any longitudinal profile or shape (e.g., they can be straight or have any desired degree of longitudinal curvature from one end of the device to the other). The trough may have any desired cross-sectional shape (e.g., the trough can be V-shaped, trapezoidal, rectangular, or other geometric shape).

To facilitate the ability of a dental treatment composition or device to conform to the various shapes and sizes among dental arches, the dental treatment composition or device may include mechanical features such as a notch within the front side wall, preferably within an edge near the center of the front side wall, and/or a notch within the rear side wall, preferably within an edge near the center of the rear side wall. Notches allow the tray-like treatment composition or device to more easily conform to differently-sized dental arches. In this way, the dental treatment composition or device can be designed so as to be "one-size fits all".

The dental treatment compositions, as well as bleaching and desensitizing devices incorporating such compositions, can be designed to be worn for any desired time period. Increasing the concentration of dental bleaching or desensitizing agent generally reduces the time it takes to bleach or desensitize teeth. Nevertheless, due to the extremely comfortable fit and reliable adhesion between the inventive dental treatment devices and the person's teeth, it is possible to wear such devices for extended periods of time in order to ensure even and thorough treatment. Dental treatment compositions according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional dental bleaching strips, which do not reliably adhere to teeth, or intrusive treatment devices such as large, bulky dental appliances.

The dental treatment compositions, as well as devices incorporating such compositions, however, can be designed to be worn for as little as a few minutes or as long as several hours. By way of example and not limitation, such compositions usually require less time to be effective and can generally be worn for short durations (10–30 minutes), intermediate durations (30 minutes–2 hours), or long durations (2–12 hours) if needed. Treatment sessions may also be repeated as many times as are needed to obtain the desired degree of bleaching and/or desensitization.

The dental bleaching and desensitizing compositions and devices included within the kits according to the invention are advantageously used together in order to effectively bleach a person's teeth while eliminating, or at least reducing, pain and discomfort that may be caused by tooth bleaching. The dental treatment compositions and devices according to the invention can be used at any time and in any order in order to bleach and desensitize teeth in a desired manner. By way of example and not limitation, a person with very sensitive teeth can utilize one or more desensitizing compositions or devices according to the invention as needed to relieve or prevent sensitivity before starting the bleaching regimen, and in between bleaching sessions as many times as needed to prevent or relieve tooth sensitivity. A person with moderately sensitive teeth might, for example, alternate between bleaching and desensitizing as desired to bleach teeth while minimizing or preventing sensitivity. A person who is not prone to having sensitive teeth may, for example, use the desensitizing compositions or devices periodically as needed to relieve sensitivity or discomfort that may arise, if at all.

For convenience of use, one or more dental bleaching compositions or device and one or more desensitizing compositions or devices are packaged together and sold as a kit. In one embodiment, the number of dental bleaching compositions or devices provided with each kit can equal the number of sessions that represent a prescribed bleaching regimen. An appropriate number of desensitizing compositions or devices are also provided with the kit in order to treat tooth sensitivity. The number of desensitizing compositions or devices may be tailored depending on need (i.e., whether or not the user is prone to having sensitive teeth).

To efficiently utilize the space within a kit package, multiple treatment compositions or devices can be stacked and interested together. The treatment compositions or devices can be sealed collectively or individually as desired. They may contain a removable protective layer on their interior surfaces to protect the active treatment layer from contamination or moisture. It is within the scope of the invention to provide barrier layers and treatment compositions that are initially separate and that are brought together by the end user. The treatment composition may be a dry or substantially solid insert or it may be a liquid or gel that is applied to the barrier and allowed to dry prior to placement of the finished dental treatment device over the person's teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
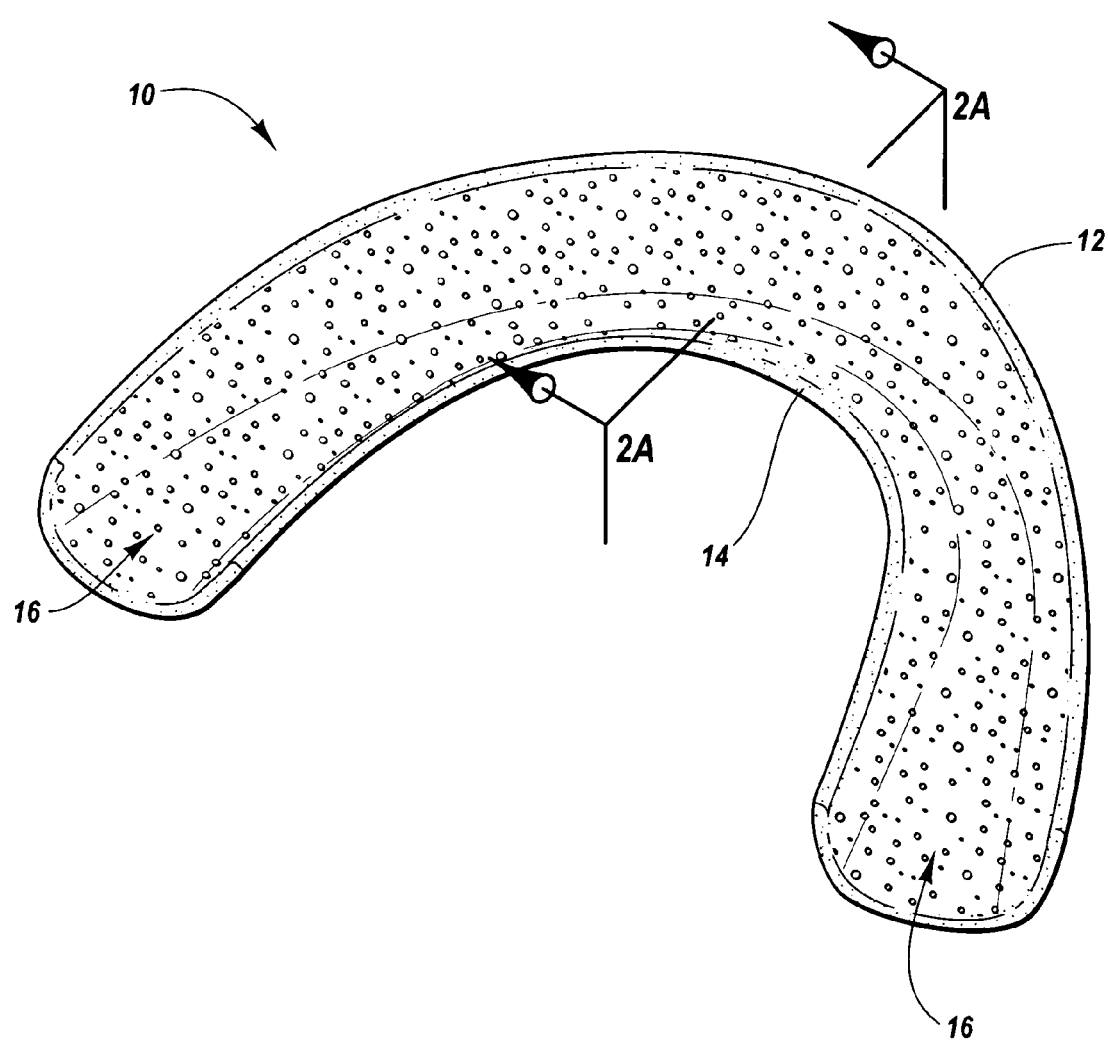
FIG. 1 is a perspective view of an exemplary dental treatment device according to the invention in the shape of a dental tray comprising a barrier layer and a substantially solid dental treatment composition.

The present invention generally relates to improved dental treatment compositions and devices used to bleach and desensitize a person's teeth, as well as kits that incorporate such treatment compositions or devices and methods for using such compositions and devices. The treatment compositions are in a substantially solid form that becomes more adhesive to teeth when moistened with water or saliva. When placed over a person's teeth, the treatment composition reliably adheres to the teeth, maintaining contact between the teeth to be treated and the dental bleaching or desensitizing agent within the treatment composition. A barrier layer may be provided that protects the dental desensitizing composition from diffusing away from the person's teeth as a result of ambient saliva or moisture found within the person's mouth.

The shaped treatment compositions and devices are more adhesive to teeth than conventional dental bleaching strips. Treatment devices according to the invention are also less intrusive than bulky, over-the-counter, non-custom or boil and bite dental trays. In some ways they are as reliable as, or even more reliable than, custom-fitted dental trays in maintaining a dental bleaching or desensitizing composition against a person's teeth. In some cases, they are also as comfortable, or even more comfortable, than custom-fitted trays.

The term "barrier layer", as used herein, refers to one or more layers of a moisture-resistant material that protects the active bleaching or desensitizing layer from ambient moisture and saliva found within a person's mouth when the dental treatment composition is placed over the person's teeth. The barrier layer may also serve to protect the treatment composition from moisture or other contaminants during storage and prior to use. The barrier layer may be in any desired form including, but not limited to, a sheet laminated to a surface of the treatment layer, a coating applied to a pre-formed treatment layer, or a dental treatment tray.

The terms "shaped bleaching composition", "shaped desensitizing composition" and "shaped treatment composition", as used herein, refer to a treatment composition that has been formulated or processed so as to be substantially solid, coherent, and non-flowable. The terms "bleaching layer", "desensitizing layer" and "treatment layer", as used herein, refer to one or more layers of a dental treatment composition that has been formulated or processed so as to be substantially solid, coherent, and non-flowable. The treatment layer may comprise a single continuous region or layer adjacent to the barrier layer, or it may comprise a plurality of discontinuous regions or layers spaced-apart by random or predetermined intervals.

The term "substantially solid", as used herein, refers to a dental treatment composition or layer that is in a solid or semi-solid condition so that it can be handled and placed against a person's teeth much like a dental tray. In one aspect, a "substantially solid" treatment composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny bleaching or desensitizing liquids, viscous bleaching or desensitizing liquids, and even thick bleaching or desensitizing gels that are able to flow when subjected to gravity and/or which can be readily expressed through a syringe outlet or other similarly-sized opening or orifice. The term "substantially solid", when used in the context of a bleaching or desensitizing composition or layer, also excludes dry particulate bleaching or desensitizing compositions or powders because dry particulates and powders readily flow when subjected to gravity and/or are readily separated (i.e., the particles as a whole have little or no internal cohesion). Moreover, powders or particulates, when viewed as a whole, are not "shaped", coherent, or solid. One characteristic of "substantially solid" treatment compositions or layers according to the invention is that they become more adhesive when an exposed surface thereof is moistened with, e.g., saliva or water. When moistened, the surface of the treatment composition or layer turns into a sticky material that is able to more strongly adhere to teeth compared to a substantially solid treatment composition or layer that has not been moistened. The composition at the surface may become a viscous liquid, paste or gel, at least temporarily, depending on the amount of moisture that is applied to the surface of the "substantially solid" treatment composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" treatment composition or layer over time (e.g., during a bleaching or desensitizing procedure in which the treatment layer or composition is protected from saliva and ambient moisture in a person's mouth by a water-proof barrier layer).

The term "dental tray", as used herein, refers to any article of manufacture or device having a tray-like shape so as to facilitate placement of the device over at least a portion of a person's dental arch. A "dental tray" or "tray-like" device includes a front side wall configured to engage front surfaces of a person's teeth when in use, a rear side wall extending laterally from the front side wall, either abruptly by one or more distinct angles or non-abruptly by a curved transition, configured to engage lingual surfaces of the person's teeth, and a trough between said front and rear side walls. A "dental tray" may be configured so that a portion of the front side wall, rear side wall, or a transition portion thereof engages the incisal or occlusal edges of the person's teeth when in use. The dental tray may be curved or straight in the longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space there between and are laterally offset by an angle of less than 180°. In practice, the front and rear side walls will be offset by an angle that is preferably less than about 150°, more preferably less than about 120°, and most preferably less than about 90°.

In the case of a trough having a U-shaped or rectangular cross section, at least a portion of the front and rear side walls may be substantially parallel (i.e., be offset by an angle of approximately 0°). In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls will be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when used to refer to a dental tray or dental treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The term "molecular weight", as used herein, refers to number average molecular expressed in Daltons unless otherwise specified.

II. Dental Treatment Compositions and Devices

The shaped dental bleaching and desensitizing compositions can exist alone or in combination with a barrier layer as part of a dental treatment device. Such dental treatment devices typically include a shaped bleaching or desensitizing composition or layer that becomes more adhesive to teeth when moistened by, e.g., saliva or water, and a moisture-resistant barrier layer that protects the treatment layer from ambient moisture within a person's mouth during use. Following are preferred examples of materials and characteristics of barrier layers and treatment compositions or layers according to the invention.

A. Barrier Layers

According to one embodiment of the invention, the barrier layer comprises a thin, flexible membrane formed from a moisture-resistant polymer material. In a preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Such materials may be provided in the form of large, flat, flexible sheets to which a bleaching or desensitizing composition or layer is applied. Alternatively, such sheets may be applied or attached to an existing bleaching or desensitizing layer comprising a substantially solid dental treatment composition.

Notwithstanding the foregoing, it is within the scope of the invention to provide barrier layers having any desired material, thickness or rigidity so long as the barrier layer provides at least some moisture protection relative to the shaped treatment composition or layer. The barrier layer may comprise a conventional dental tray, examples of which include both customized and non-custom dental trays. The barrier layer may be as simple as a layer of a moisture resistant material that is sprayed or painted on, applied by dipping, or otherwise applied to an existing treatment composition (e.g., one that is in the form of a dental tray or that otherwise has a desired shape).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. Plasticizers, flow additives, and fillers known in the art can be used as desired to modify the properties of any of the foregoing polymers used to form the barrier layer.

As will be discussed below, some dental treatment compositions will be more adhesive to polymer materials comprising the barrier layer than others, often depending on the tooth adhesion agent that is used. It has been found that, as between polyethylene, paraffin and polyethylene terephthalate, substantially solid dental treatment compositions tend to adhere more strongly to polyethylene terephthalate, particularly MYLAR.

It is also within the scope of the invention to utilize barrier layers that are formed onto a surface of a previously formed bleaching or desensitizing composition, such by adhering a sheet or tray-like barrier layer to the treatment composition, which may then be thought of as a "treatment layer" (i.e., a "bleaching layer" or "desensitizing layer"). Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose, butyl cellulose, t-butyl cellulose, and the like.

B. Substantially Solid Treatment Compositions and Layers

The substantially solid bleaching and desensitizing compositions according to the invention can be in the shape of a dental tray, with or without a barrier layer. Where a barrier layer is present, the solid treatment composition may be thought of as a treatment layer. Prior to being moistened in preparation for or during use, treatment compositions or layers according to the invention preferably comprise a substantially solid and coherent dental treatment composition, as opposed to a liquid, a flowable gel, or a dry powder or particulate treatment composition. In the case of a bleaching or desensitizing device, the treatment layer may comprise a single coherent mass or region, or it may comprise a plurality of coherent masses or regions of a substantially solid treatment composition adhered to the barrier layer. Providing a substantially solid and coherent treatment layer better maintains the treatment composition between the barrier layer and the teeth being treated instead of diffusing into the surrounding oral cavity, as compared to conventional bleaching or desensitizing gels that are loaded into customized or non-customized dental trays. This, in turn, promotes better bleaching and desensitization, as well as patient compliance.

Substantially solid dental treatment compositions and layers according to the invention include at least one bleaching or desensitizing agent and at least one tooth adhesion agent. In a preferred embodiment, the bleaching or desensitizing agent is dispersed within a substantially solid matrix comprising the tooth adhesion agent. In one embodiment, a dental bleaching agent may optionally be combined with a desensitizing agent to form a bleaching composition that has decreased sensitivity. Following are preferred bleaching, desensitizing, and tooth adhesion agents.

1. Bleaching Agents

A common dental bleaching agent that is known to bleach teeth and that has been found to be safe for oral use is hydrogen peroxide. However, hydrogen peroxide does not itself exist free in nature, but only as an aqueous solution or as a complex. Preferred dental bleaching agents comprise complexes of hydrogen peroxide because they are more stable than aqueous hydrogen peroxide, which tends to be unstable when heated, especially when water is removed by evaporation.

Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within the substantially solid dental bleaching compositions according to the invention can have any desired concentration, e.g., between 1–90% by weight of the substantially solid dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

The one or more bleaching agents are preferably included in an amount in a range of about 5% to about 80% by weight of the substantially solid dental bleaching composition, more preferably in a range of about 10% to about 60% by weight of the substantially solid dental bleaching composition, and most preferably in a range of about 20% to about 50% by weight of the substantially solid dental bleaching composition.

2. Desensitizing Agents

A common dental desensitizing agent that is known to desensitize teeth and that has been found to be safe for oral use is potassium nitrate. Other desensitizing agents that can be used to desensitize teeth include, but are not limited to, other potassium salts, citric acid, citrates, strontium chloride, stannous fluoride, and sodium fluoride.

Desensitizing agents within the substantially solid dental desensitizing compositions according to the invention can have any desired concentration, e.g., between 0.01–50% by weight of the substantially solid dental desensitizing composition. The concentration of the dental desensitizing agent can be adjusted depending on the intended treatment time for each desensitizing session. In general, the shorter the treatment time, the more desensitizing agent will be added to accelerate dental desensitizing so as to effect desensitizing in a shorter time period.

In a preferred embodiment, potassium nitrate is the preferred desensitizing agent and is preferably included in an amount in a range of about 0.01 to about 50% by weight of the substantially solid dental desensitizing composition, more preferably in a range of about 0.1% to about 25% by weight of the substantially solid dental desensitizing composition, and most preferably in a range of about 0.5% to about 10% by weight of the substantially solid dental desensitizing composition.

Embodiments including other desensitizing agents instead of potassium nitrate, such as but not limited to, other potassium salts, citric acid, citrates, strontium chloride, sodium fluoride, and stannous fluoride, preferably include such agents in an amount in a range of about 0.1 to about 10% by weight of the substantially solid dental composition, and most preferably in a range of about 1–7% by weight of the substantially sold dental desensitizing composition.

In embodiments combining desensitizing agent potassium nitrate with a bleaching agent, such as but not limited to hydrogen peroxide, the desensitizing agent is preferably included in an amount in a range of about 0.01 to about 2% by weight of the substantially solid dental desensitizing composition, more preferably in a range of about 0.05% to about 1% by weight of the substantially solid dental desensitizing composition, and most preferably in a range of about 0.5% by weight of the substantially solid dental desensitizing composition. It has been found that including potassium nitrate within these ranges creates a synergistic effect with the dental bleaching agent that appears to enhance tooth whitening. It also provides the highest level of tooth desensitization when used with a bleaching agent.

3. Tooth Adhesion Agents

The tooth adhesion agent may comprise any known tackifying agent that is substantially non-adhesive, or less adhesive, when the dental treatment composition is substantially solid but which becomes more adhesive to teeth when the dental treatment composition is moistened with, e.g., water or saliva. A presently preferred tooth adhesion agent is polyvinyl pyrrolidone (PVP). PVP polymers have been found to provide excellent adhesion to polymer barrier layers made from PE, PET and paraffin, to be substantially non-adhesive when the dental treatment composition is dry to the touch, and to have superior adhesion to teeth when a surface of a substantially solid dental treatment composition is moistened with saliva or water.

Non-limiting examples of polyvinyl pyrrolidone polymers that may be useful in formulating bleaching and desensitizing compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid treatment compositions or layers according to the invention.

Other tooth adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tooth adhesion agent, it has been found that a polyethylene oxide polymer having a molecular weight of 1 million provides better adhesion to barrier layers such as MYLAR than a polyethylene oxide polymer having a molecular weight of 100,000.

The one or more tooth adhesion agents are preferably included in an amount in a range of about 10% to about 90% by weight of the substantially solid bleaching or desensitizing composition (exclusive of any bound water or other solvent), more preferably in a range of about 20% to about 80% by weight of the substantially solid bleaching or desensitizing composition, and most preferably in a range of about 40% to about 75% by weight of the substantially solid bleaching or desensitizing composition.

4. Other Components

The dental treatment compositions and layers may include other components as desired to yield a final composition or layer having desired properties. Examples of other components include, but are not limited to, plasticizers and humectants (e.g., glycerin, sorbitol, and polyethylene glycol), volatile solvents (e.g., water and alcohols, such as ethanol), stabilizing agents (e.g., EDTA), neutralizing agents (e.g., sodium hydroxide), thickening agents (e.g., fumed silica), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

When water is used as a solvent when manufacturing bleaching or desensitizing compositions or layers according to the invention and then driven off by evaporation to yield a substantially solid dental bleaching or desensitizing composition, it is postulated that a significant amount of water remains bound or associated with the hydrophilic components within the treatment composition, including the bleaching and/or desensitizing agent, the tooth adhesion agent, and any polyols added as humectants. Although the amount of residual water has not yet been determined, it is believed that approximately 10% of the water added initially remains after the initially flowable dental treatment composition has been dried sufficiently to yield a substantially solid bleaching or desensitizing composition.

C. Characteristics of Dental Treatment Compositions and Treatment Devices Incorporating Such Compositions Dental bleaching or desensitizing compositions according to the invention, as well as treatment devices incorporating such compositions, are preferably in the shape of a dental tray having a front side wall, a rear side wall, and a trough between the front and rear side walls. Having the shape of a dental tray facilitates placement of the dental treatment composition or device over a person's teeth by reducing the amount of manipulation that is necessary to obtain a good fit between the device and the person's teeth.

Dental treatment compositions and desensitizing devices in the shape of a dental tray it that comprise a substantially solid treatment composition that becomes more adhesive when moistened with water or saliva are easier to install over a person's teeth compared to dental bleaching strips or patches, which are initially flat and which must be manipulated so as to wrap the initially flat strip or patch around the occlusal or incisal edges of the teeth in order to cover the front and lingual tooth surfaces. In addition, the inventive dental treatment compositions and devices are designed to more reliably adhere and remain in place over the person's teeth compared to conventional bleaching strips, which employ a dental bleaching gel that is already flowable prior to placing the strip over a person's teeth to be treated. The result is more effective tooth bleaching and desensitizing, as well as better patient compliance. In contrast to conventional bleaching strips, which are not recommended for use while a person eats, drinks, smokes or sleeps, dental treatment compositions and devices according to the invention can be designed so as to be worn while talking, sleeping, eating, drinking, smiling, frowning, grimacing, yawning, coughing, smoking, or making virtually any facial expression or mouth contortion.

Figure 2A:
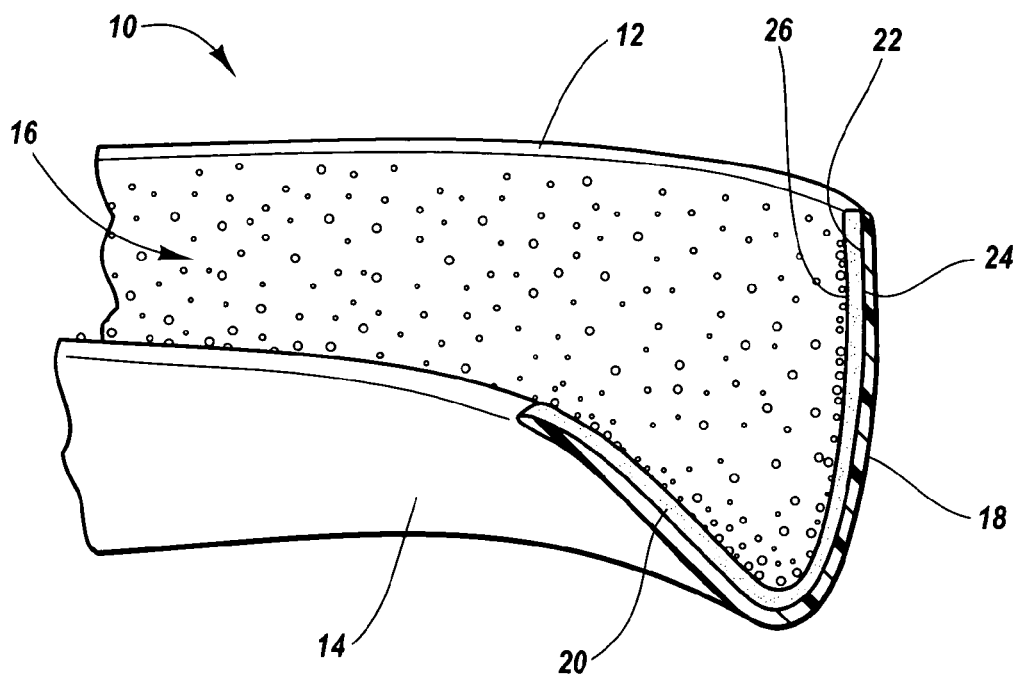
FIG. 2A is a cross-sectional view of the dental treatment composition or device depicted in FIG. 1A.

According to one currently preferred embodiment, the dental treatment compositions and devices have a horseshoe shaped longitudinal profile and a trough with a U-shaped cross section, much like a conventional dental tray. An exemplary dental treatment device is depicted in FIGS. 1 and 2A. FIG. 1 is a perspective view of a dental treatment device 10 having a front side wall 12 and a rear side wall 14 that together have a generally horseshoe shape in a longitudinal dimension and that define a trough 16 having a generally U-shaped cross section. The U-shaped cross section of the trough is seen even more clearly in FIG. 2A.

The dental treatment device 10 further includes a barrier layer 18, preferably comprising a moisture-resistant material, and a coherent treatment layer 20, preferably comprising a substantially solid dental bleaching or desensitizing composition. As best seen in FIG. 2A, the bleaching or desensitizing layer 20 includes an exterior surface 22 disposed adjacent to an interior surface 24 of the barrier layer 18 and an interior treatment surface 26 designed to directly contact a person's teeth when the dental treatment device 10 is in use. An upper edge 28 of the barrier layer 18 can be designed so as to terminate at or shy of the gingival margin of a person's dental arch when in use.

Figure 2B:
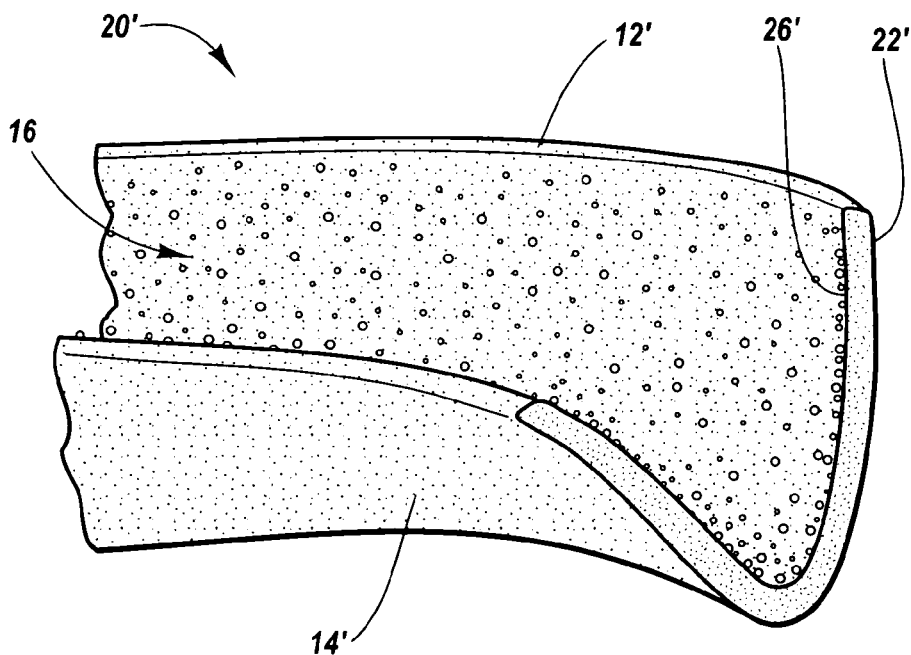
FIG. 2B is a cross-sectional view of an exemplary dental treatment composition according to the invention in the shape of a dental tray without a barrier layer.

FIG. 2B alternatively depicts a dental treatment composition 20' (i.e., a dental bleaching composition or desensitizing composition) in the shape of a dental tray so as to have a front side wall 12' and a rear side wall 14' but with no barrier layer. The treatment composition 20' includes an interior treatment surface 26' designed to directly contact a person's teeth when the treatment composition 20' is in use and an exterior surface 22' that may optionally be coated with a water-resistant barrier layer or material if desired to protect the treatment composition 20' from saliva (see FIG. 2A). The treatment composition 20' may be sold alone or together with a barrier layer or material.

Figure 3:
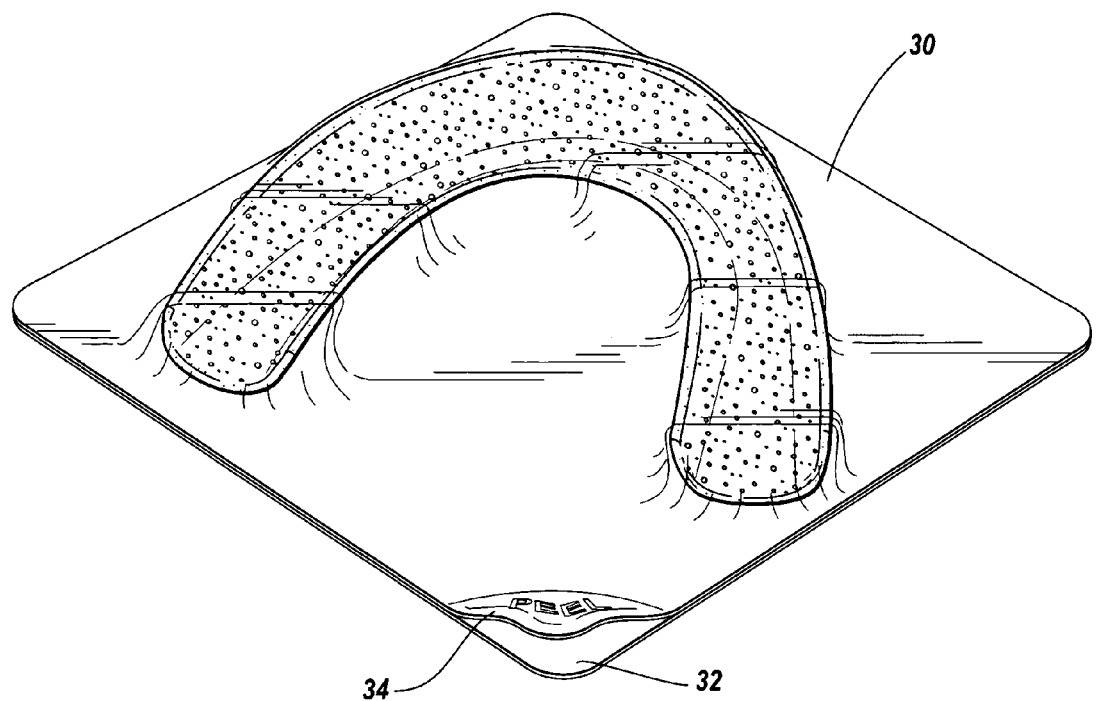
FIG. 3 illustrates a dental treatment device contained within a sealed protective package having a peelable cover.

In order to protect dental bleaching and desensitizing compositions and devices according to the invention from contaminants during storage and prior to use, the treatment devices and compositions can be packaged within a sealed container or package. As illustrated in FIG. 3, the dental treatment device 10 can be sealed within a protective package 30 that includes a rigid support layer 32 and a peelable cover 34. When it is desired to use the dental treatment device 10 to bleaching and/or desensitize teeth, the peelable cover 34 is removed and the treatment device 10 is removed or separated from the support layer 32. In addition to, or instead of, the protective package 30, the dental treatment device 10 may alternatively include a removable protective layer (not shown) that is temporarily placed adjacent to the interior treatment surface 26 of the treatment layer 20. When it is desired to use the dental treatment device 10 to bleach and/or desensitize teeth, the removable protective layer is removed so as to expose the interior treatment surface 20.

The protective package 30 or other protection means may also be used to protect shaped treatment compositions that do not include a barrier layer, such as the treatment composition 20' depicted in FIG. 2B.

Figure 4:
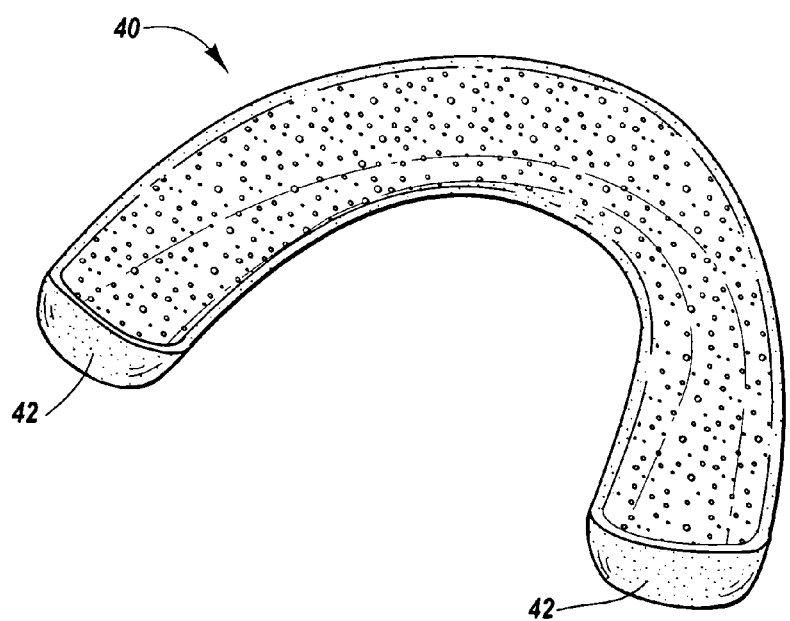
FIG. 4 is a perspective view of an exemplary dental treatment composition or device that is similar to the treatment device depicted in FIG. 1, or the treatment composition of FIG. 2B, but that further includes a terminal side wall on each longitudinal end.

FIG. 4 illustrates a dental treatment composition or device 40 that is a variation of the U-shaped dental desensitizing device 10 of FIGS. 1 and 2A or the treatment composition 20' shown in FIG. 2B. The main difference is that each longitudinal end 42 of the dental treatment composition or device 40 is raised so as to at least partially enclose the last tooth on each side of a person's dental arch when the treatment composition or device 40 is in use.

Figure 5:
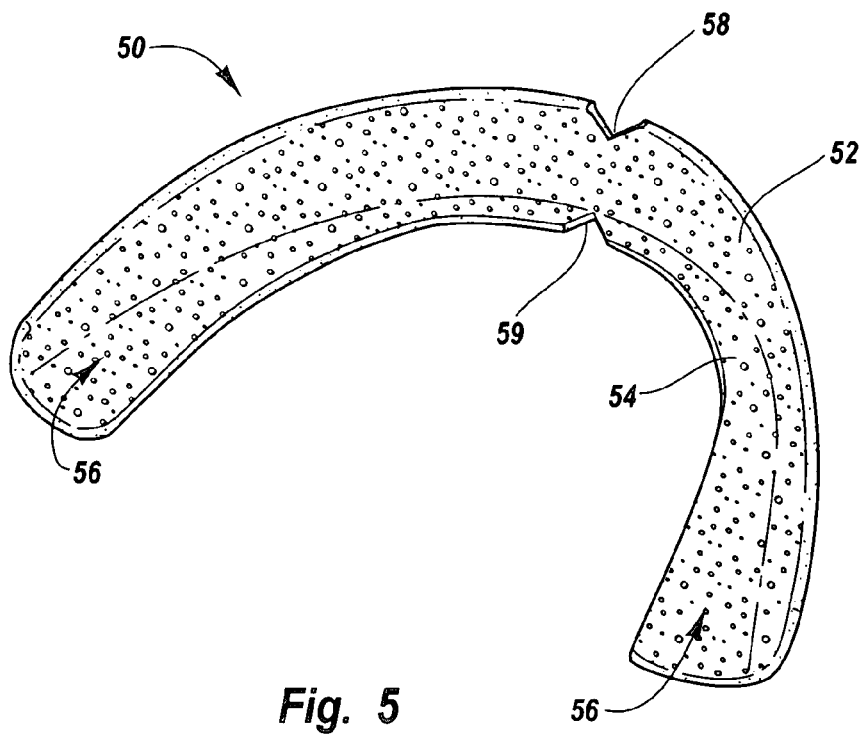
FIG. 5 is a perspective view of an exemplary dental treatment device having an L-shaped trough and a curved longitudinal profile.

FIG. 5 illustrates an alternative embodiment of a dental treatment composition or device 50 according to the invention that is L-shaped. More particularly, the dental treatment composition or device 50 includes a front side wall 52 and a rear side wall 54 extending laterally from the front side wall 52 so as to form a trough 56 having an approximate L-shaped cross section. The L-shaped treatment composition or device 50 of FIG. 5 is somewhat easier to initially place over a person's dental arch compared to the U-shaped treatment compositions or devices of FIGS. 1–4. This is due to the approximately planar orientation of the rear side wall 54 relative to the occlusal or incisal edges of a person's teeth when the front side wall 52 of the treatment composition or device 50 is initially placed and adhered against the front surfaces of a person's teeth. On the other hand, more manipulation of an L-shaped bleaching or desensitizing device is generally required to form and adhere the rear side wall 54 against the lingual surfaces of the person's teeth as a result of the greater initial offset angle between the front side wall 52 and rear side wall 54. However, the ability of treatment compositions and devices according to the invention to adhere to tooth surfaces almost immediately, or within a few seconds, after being wetted facilitates the process of conforming the front side wall 52 and rear side wall 54 to the person's tooth surfaces.

In the case of the dental treatment composition or device 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped bleaching or desensitizing composition or device is folded back against the lingual tooth surfaces during use, it can be readily seen that a treatment composition or device having an L-shaped trough is merely a variation of a composition or device having a V-shaped trough. Thus, for purposes of this disclosure and the appended claims, the side wall 54 shall constitute, and fall within the definition of, a "rear side wall".

To facilitate the ability of a dental treatment composition or device to conform to the varying shapes and sizes among dental arches, the composition or device may include mechanical features such as one or more notches within the front or rear side walls. As shown in FIG. 5, the dental treatment composition or device 50 includes a notch 58 in an outer edge near the center of the front side wall 52 and a notch 59 in an outer edge near the center of the rear side wall 54. Notches 58 and 59 allow the tray-like treatment composition or device to more easily spread open or compress when being conformed to differently-sized dental arches. In this way, the dental treatment composition or device 50 can more easily be a "one-size fits all" device.

Figure 6:
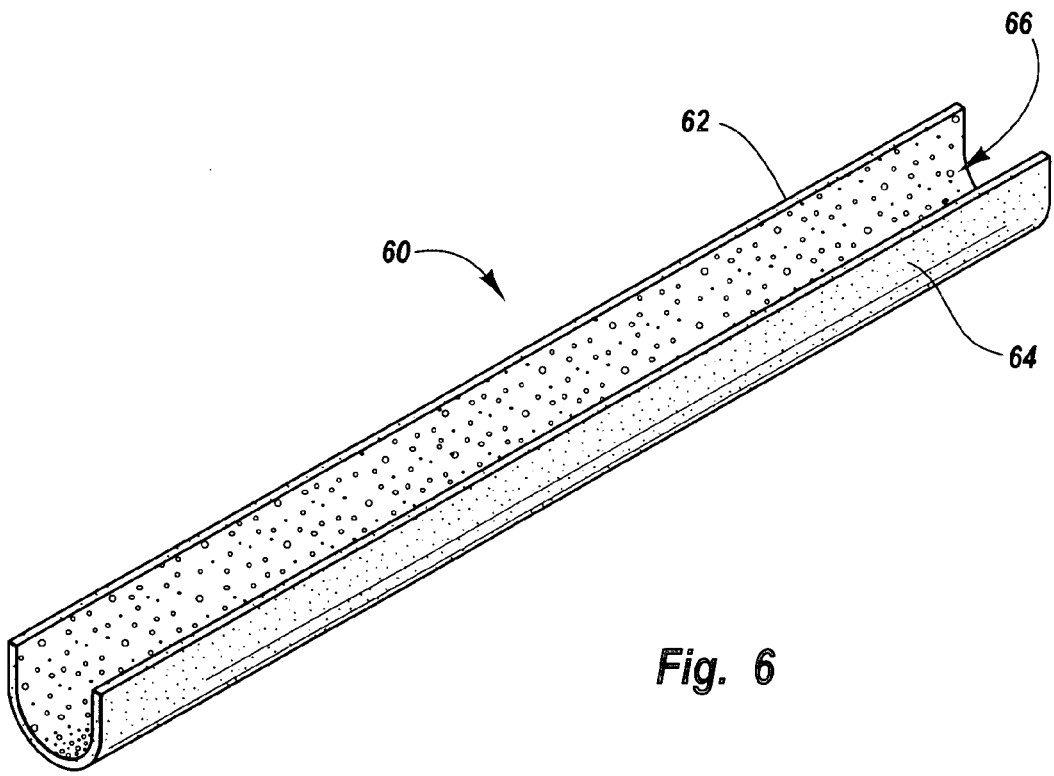
FIG. 6 is a perspective view of an exemplary dental treatment composition or device having a U-shaped trough and a substantially straight longitudinal profile.

FIG. 6 depicts an alternative embodiment of a dental treatment composition or device 60 according to the invention, which includes a front side wall 62 and a rear side wall 64 that define a U-shaped trough 66. Instead of being horseshoe shaped like the dental treatment compositions or device of FIGS. 1–5, or otherwise having a curved longitudinal profile, the dental treatment composition or device 60 of FIG. 6 has a substantially straight or linear longitudinal profile.

Figure 7:
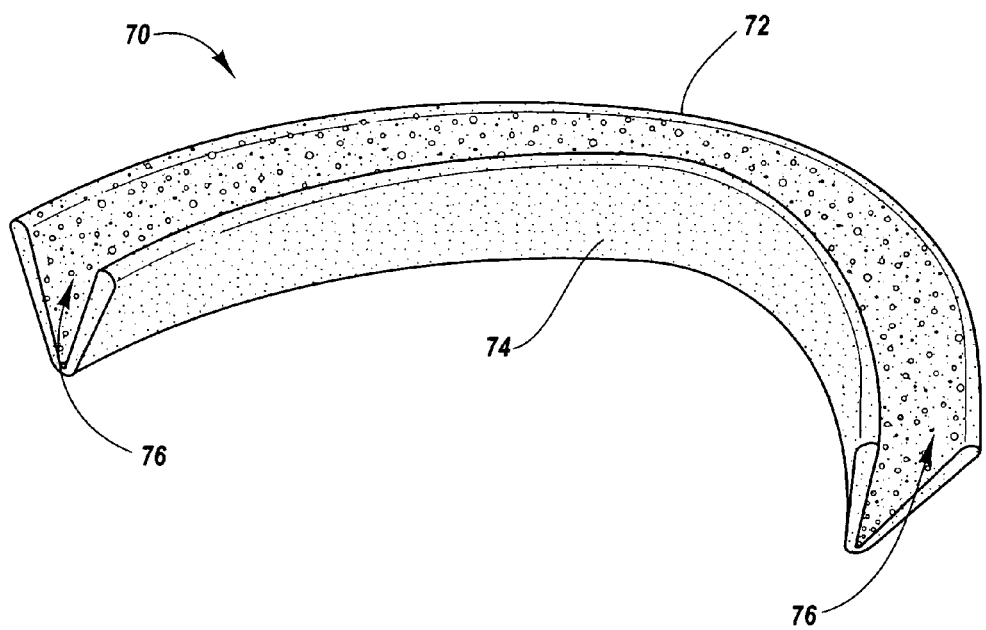
FIG. 7 is a perspective view of an exemplary dental treatment composition or device having a V-shaped trough and a curved longitudinal profile.

FIG. 7 depicts yet another alternative embodiment of a dental treatment composition or device 70 according to the invention. The dental treatment composition or device 70 includes a front side wall 72 and a rear side wall 74 that define a V-shaped trough 76 and a curved longitudinal profile. The main difference between the V-shaped treatment composition or device 70 of FIG. 7 and the L-shaped treatment composition or device 50 of FIG. 5 is the angle at which the front and rear side walls are laterally offset from each other.

Notwithstanding the foregoing examples, it will be appreciated that dental treatment compositions and devices according to the invention can have any longitudinal shape (e.g., they can have a straight or curved longitudinal profile from one end to the other). The front and rear side walls may define a trough of any desired cross-sectional shape (e.g., the trough can be trapezoidal, rectangular, or any other desired geometric shape).

The size and shape of dental bleaching and desensitizing compositions according to the invention, as well as bleaching and desensitizing devices incorporating such compositions, can be tailored to more readily fit either a person's upper dental arch or lower dental arch. They can be sized so as to bleach or desensitize all or merely a subset of a person's teeth. The dental treatment composition or device may be sufficiently adhesive and flexible so as to readily conform to a wide variety of differently-sized teeth and dental arches. The dental treatment compositions or devices are advantageously designed so as to substantially cover the front and lingual surfaces of the teeth to be bleached or desensitized. Bleaching and desensitizing both surfaces yields a more even treatment, although it is certainly within the scope of the invention to desensitize one surface or more of one surface than another. Bleaching both the front and back surfaces of a person's teeth also helps to more completely bleach the interproximal spaces between a person's teeth. If left unbleached, stained interproximal spaces can form a dark ring or silhouette around each tooth.

In general, the thickness of the barrier layer and/or the treatment composition of a treatment device can be adjusted to yield a treatment device having a desired strength and flexibility. In order for the barrier layer to remain flexible so as to conform to a person's teeth, the barrier layer will preferably have a thickness ranging from about 0.025 mm to about 1.5 mm, more preferably in a range of about 0.5 mm to about 1.25 mm, and most preferably in a range of about 0.1 mm to about 1 mm.

The shaped bleaching and desensitizing compositions or layers according to the invention will generally have a thickness ranging from about 0.1 mm to about 3 mm. The thickness of the desensitizing composition or layer can also be selected depending on the intended duration of each bleaching or desensitizing session. In general, increasing the thickness of the treatment composition or layer will provide a longer or more sustained release of active dental agent. By way of example, for short wear times, the treatment composition or layer will preferably have a thickness ranging from about 0.1 mm to about 0.5 mm. For intermediate wear times, the treatment composition or layer will preferably have a thickness ranging from about 0.5 mm to about 2 mm. For overnight treatments, the treatment composition or layer will preferably have a thickness ranging from about 2 mm to about 3 mm.

III. Method of Making Substantially Solid Dental Bleaching and Desensitizing Compositions and Treatment Devices Incorporating Such Compositions According to one embodiment, the dental bleaching or desensitizing compositions or layers according to the invention are made by first forming a flowable bleaching or desensitizing composition that is later dried to form a substantially solid treatment composition or layer. This may be performed by heating or otherwise causing one or more volatile solvents to be driven off by evaporation, thus leaving behind a substantially solid treatment composition or layer. The drying process may be performed before or after the treatment composition or layer is placed into contact with a barrier layer.

According to one embodiment, substantially solidified dental treatment compositions and devices can be made by spreading a flowable precursor composition onto the surface of a large or continuous polymeric sheet (e.g., using a screeding device). The polymeric sheet and precursor composition are then placed into a forced air oven or other appropriate desiccation device in order to heat and drive off a substantial portion of the water or other solvent used to form the flowable precursor composition. Removal of the volatile solvent yields a treatment layer comprising a substantially solid bleaching or desensitizing composition. Thereafter, individual tray-like dental treatment devices can be molded, such as by vacuum forming, pressing or stamping from the coated polymeric sheet and then separated into individual treatment devices suitable for placement over a person's teeth.

Alternatively, the substantially solid treatment composition can be separated from the polymeric sheet and then molded, stamped or otherwise formed into a desired shape of a dental treatment composition.

Alternatively, a flowable or substantially solid dental treatment composition can be molded or shaped into a desired tray-like configuration comprising the treatment composition or layer. Thereafter, a barrier layer may optionally be attached or applied to an outer surface of the shaped treatment composition or layer. In this embodiment, the barrier layer may comprise a solid polymeric sheet or other barrier material, or it may initially comprise a flowable barrier material or precursor that is later cured or hardened, such as by removing a solvent by evaporation, by chemical or light curing, or by cooling a thermoplastic melt.

In yet another embodiment of the invention, a barrier layer in the form of a dental tray or tray-like device (e.g., a customized or non-custom tray) can be coated with a flowable dental treatment composition. The treatment composition is then heated together with the dental tray or otherwise allowed to dry in order to form a shaped treatment layer comprising a substantially solid bleaching or desensitizing composition. This process can be performed during commercial manufacture of the treatment device or by an end user.

IV. Methods of Using Dental Bleaching and Desensitizing Compositions and Treatment Devices Incorporating Such Compositions The dental bleaching and desensitizing compositions according to the invention, as well as treatment devices incorporating such compositions, can be designed to be worn for any desired time period. Increasing the concentration of dental bleaching or desensitizing agent generally reduces the time required to effect bleaching or desensitization. Nevertheless, due to the extremely comfortable fit and reliable adhesion between the inventive treatment compositions or devices and the person's teeth, it is possible to wear such compositions or devices for extended periods of time in order to ensure more uniform bleaching and/or desensitization. They may be designed to be worn while performing normal daily activities, such as talking, eating, drinking, smoking, coughing, smiling, frowning, grimacing, or while sleeping. This greatly decreases their intrusiveness into everyday activities compared to, e.g., conventional bleaching strips, which do not reliably adhere to teeth, or intrusive devices such as large, bulky dental appliances.

The dental treatment compositions or devices according to the invention may be worn over a person's upper dental arch, lower dental arch, or both simultaneously. The ability to reliably and comfortably wear the treatment compositions or devices over the upper and lower dental arches simultaneously is another departure from bleaching strips, which are not recommended for use in the upper and lower dental arches at the same time.

Figure 8:
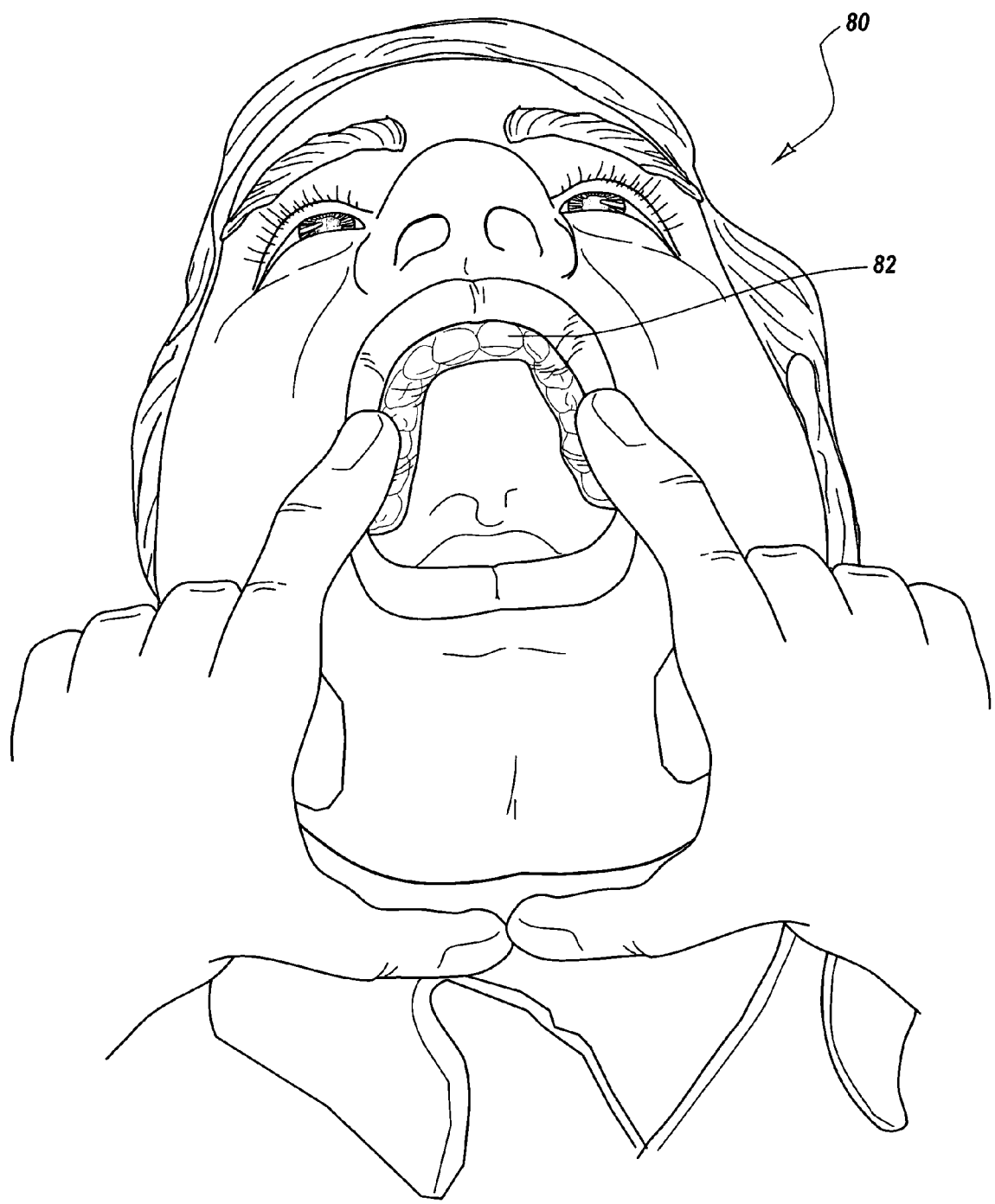
FIG. 8 illustrates a person placing a dental treatment composition or device according to the invention over the upper dental arch.
Figure 9:
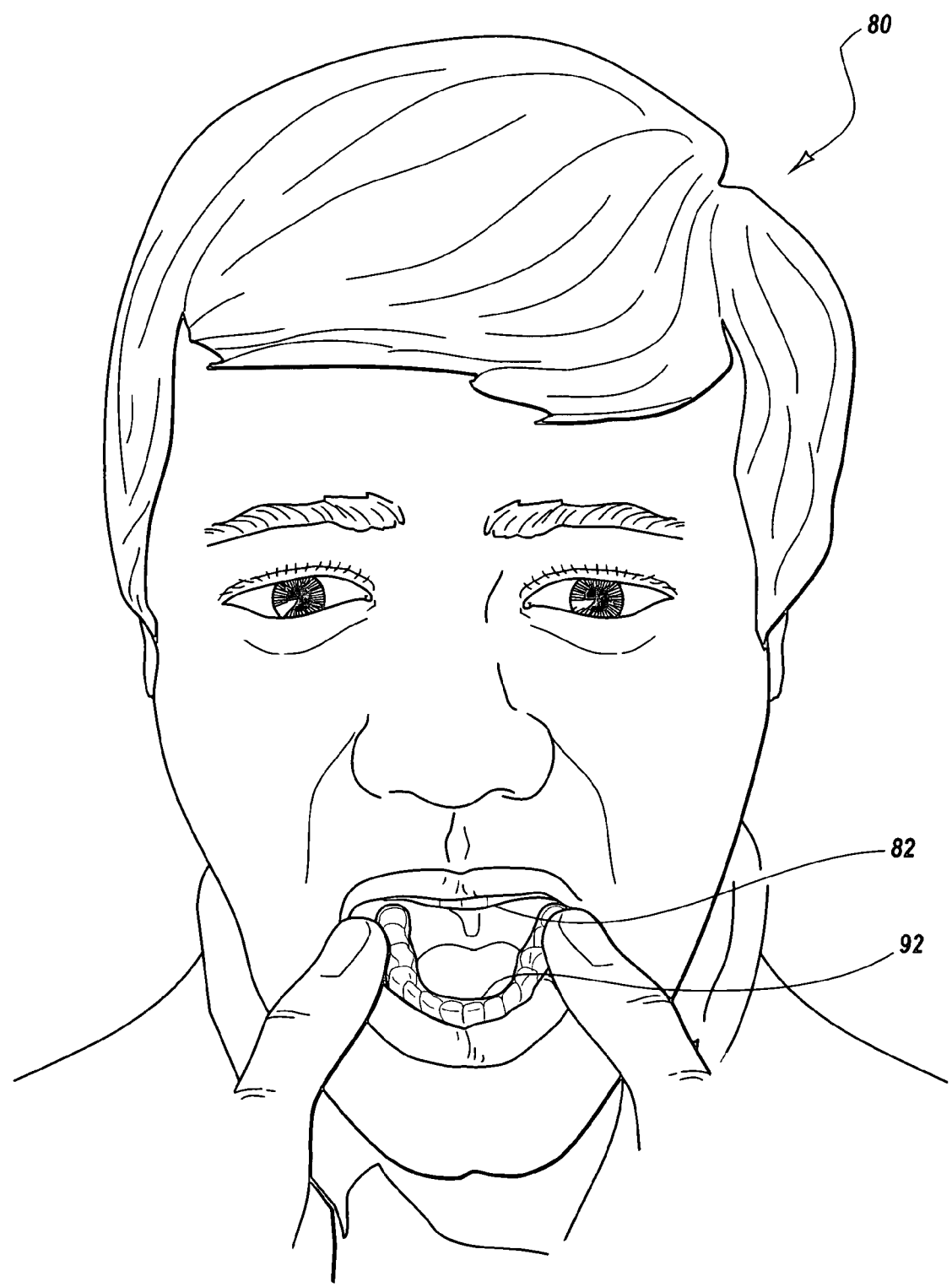
FIG. 9 illustrates a person placing a dental treatment composition or device according to the invention over the lower dental arch, with a dental treatment composition or device already placed over the upper dental arch.

FIG. 8 illustrates a person 80 placing a dental treatment composition or device 82 over the person's upper dental arch. FIG. 9 illustrates the person 80 placing a dental treatment composition or device 92 over the person's lower dental arch after having placed the treatment composition or device 82 over the upper dental arch. It will be appreciated, however, that the dental treatment compositions or devices can be placed over a person's upper and lower dental arches in any desired order.

To remove the treatment composition or device, a user can pry open a corner of the barrier layer or desensitizing composition using a fingernail or rigid tool and then pull the remainder off. Any residual bleaching or desensitizing composition or layer that remains adhered to the person's teeth can be removed by washing or flushing water over the person's teeth, and/or by brushing. Although the inventive dental treatment compositions are very adhesive to teeth when protected from excessive moisture, they can be formulated to quickly break down and dissolve when flushed with excess water and/or by gentle mechanical action (e.g., brushing).

The dental treatment compositions or devices can be worn for as little as a few minutes and as long as several hours. By way of example, not limitation, a typical bleaching or desensitization session of short duration may last from about 10 to about 30 minutes. A bleaching or desensitizing session of intermediate duration may last from about 30 minutes to about 2 hours. A bleaching or desensitizing session of long duration, including overnight desensitizing while a person is sleeping, may last from about 2 hours to about 12 hours.

The bleaching and desensitizing sessions according to the invention may be repeated as many times as are needed to obtain a desired degree of bleaching and desensitization. In some cases, a clinical effect has been observed after only 1–3 bleaching or desensitizing sessions. A typical bleaching regimen will preferably include 1–20 bleaching sessions, more preferably 2–15 bleaching sessions, and most preferably 3–10 bleaching sessions. The number of desensitization sessions that are carried out in conjunction with the bleaching sessions may vary greatly depending on the amount of sensitivity, if any, experienced by the user. A typical desensitization regimen will preferably include 1–20 desensitization sessions, more preferably 2–15 desensitization sessions, and most preferably 3–10 desensitization sessions.

The dental desensitizing compositions or devices may be used preliminarily to applying the dental bleaching compositions or devices, subsequent to applying the dental bleaching compositions or devices, or simultaneous with applying a dental bleaching composition. In the latter case, the dental bleaching composition may be in the form of a gel or liquid that can be placed into the tray-like desensitizing device.

V. Dental Treatment Kits

For convenience of use, one or more dental bleaching compositions or devices may be may be packaged together and sold as a kit together with one or more dental desensitizing compositions or devices. In one embodiment, the number of dental bleaching compositions or devices provided with each kit will equal the number of sessions that represent a prescribed bleaching regimen. Because of the ease of placing the inventive dental bleaching compositions or devices over a person's teeth, coupled with the reliability with which they achieve adhesion to teeth, the likelihood that a particular bleaching composition or device will not work as intended or fail is greatly decreased compared to conventional bleaching strips. The number of desensitizing compositions or devices may be selected depending on the how sensitive a person's teeth are.

For example, people with very sensitive teeth may wish to purchase a kit that includes a relatively large number of desensitizing compositions or devices (e.g., a number that equals or exceeds the number of bleaching compositions or devices in the kit). People with moderately sensitive teeth may wish to purchase a kit that includes a moderate number of desensitizing compositions or devices (e.g., from half up to the number of bleaching compositions or devices in the kit). People with teeth that are not prone to sensitivity may wish to purchase a kit that includes a smaller number of desensitizing compositions or devices (e.g., from one up to half to the number of bleaching compositions or devices in the kit). One purpose for modifying the relative number of desensitizing compositions or devices in a particular kit to reflect the amount of desensitization that is required is to reduce the cost and bulkiness of the kit where less desensitization is necessary.

To efficiently utilize the space within a kit package, multiple dental bleaching and/or desensitizing compositions or devices can be stacked or interested together. The dental treatment compositions or devices can be sealed collectively or individually as desired. A protective package 30 is depicted in FIG. 3. The treatment composition or layer may optionally contain a removable protective layer on an interior surface to protect the bleaching or desensitizing composition or layer from contamination or moisture.

It is within the scope of the invention to provide barrier layers and shaped treatment compositions that are initially separate and that are brought together by the end user. For example, the shaped bleaching and/or desensitizing compositions may be a substantially solid insert that is placed into a customized or non-custom tray, that is coated with an initial flowable barrier material, or that is covered with a flexible barrier sheet. Alternatively, a flowable dental bleaching and/or desensitizing composition can be placed within the trough of a tray-like barrier layer and allowed to solidify so as to yield a shaped dental treatment composition or layer.

VI. Examples of the Preferred Embodiments

The following are several examples of dental bleaching and desensitizing compositions that have been formulated and manufactured according to the invention. Such exemplary formulations and manufacturing conditions are given by way of example, and not by limitation, in order to illustrate dental bleaching and desensitizing compositions that have been found to be useful for bleaching and desensitizing a person's teeth. Unless otherwise indicated, all percentages are by weight.

EXAMPLE 1

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| Polyvinyl pyrrolidone (M.W. = 1.3 million) | 38% |
| Water | 46% |

The resulting bleaching composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The bleaching composition was spread using a spatula. The coated sheets were heated in a forced air oven heated to a temperature of 50–70° C. for approximately 1 hour. The coated sheets were removed from the oven and inspected. The bleaching composition had dried sufficiently so as to form a solid, coherent bleaching layer on the surface of the polymer sheets. The dried bleaching composition adhered well to each of the polymer sheets. The coated sheets were placed back into the oven overnight to remove additional water.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch.

The tray-like dental bleaching devices were tested by placing them over a person's teeth. The residual saliva present on the tooth surfaces moistened the exposed surface of the dry dental bleaching composition and caused it to become sticky and very adhesive to teeth almost immediately. The bleaching devices were pressed against the teeth, which caused them to conform to the natural irregularities of the dental arch and adhere firmly against the teeth.

The tray-like dental bleaching devices were worn for varying time periods ranging from several minutes to several hours without becoming dislodged. The formation of oxygen bubbles within the moistened bleaching composition against the person's teeth indicated that the peroxide bleaching agent remained active and was suitable for bleaching teeth even after the bleaching composition was heated overnight in an oven. In some cases a noticeable bleaching effect was detected after just one bleaching session (e.g., a 2-hour bleaching session). In all cases, noticeable bleaching was detected after 1–3 bleaching sessions.

EXAMPLE 2

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| PolyOx WSR 101 (M.W. = 1 million) | 7% |
| Water | 77% |

The resulting bleaching gel was spread over the surface of MYLAR sheets using a spatula. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. Unlike the bleaching composition of Example 1, the dried bleaching composition did not adhere strongly to the polymer sheets but was easily separated from the sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch.

The tray-like dental bleaching devices were tested by placing them over a person's teeth. The residual saliva present on the tooth surfaces moistened the exposed surface of the dry dental bleaching composition and caused it to become sticky and adhesive to teeth within a few seconds. The results of Example 2 indicate that, while polyethylene oxide was a satisfactory teeth adhesion agent, it was less satisfactory in promoting adhesion between a dried dental bleaching composition and a polymer sheet.

EXAMPLE 3

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| Carbopol 974P | 5% |

-continued

| | |
|---|---|
| Aqueous NaOH (50%) | 6% |
| Water | 73% |

The resulting bleaching gel was spread over the surface of MYLAR sheets using a spatula. The coated sheets were heated in a forced air oven heated to a temperature of 50–70° C. for approximately 1 hour. The coated sheets were removed from the oven and inspected. Although the bleaching composition dried sufficiently to form a solid, it shrunk considerably, probably because of the large amount of water that was needed to cause Carbopol to form a gel. Shrinkage of the bleaching composition caused the polymer sheet to become partially shriveled up. Whereas shriveling of the polymer sheet was not desired, using carboxypolymethylene as a tooth adhesion agent resulted in a dried bleaching composition that adhered to a polymer sheet.

Thereafter, the coated sheets were removed from the oven after heating overnight, cut apart into smaller-sized pieces, and shaped into tray-like dental bleaching devices suitable for placement over a person's teeth. When placed over a person's teeth it took about 5 seconds for the dental bleaching composition to become moistened enough to start becoming sticky and adhesive to teeth. The dental treatment device was able to conform to the person's teeth and remain in place after being pressed against the teeth for about 30–60 seconds.

The results of Example 3 indicate that, while Carbopol 974 P is able to adhere to a MYLAR sheet and appears to be a satisfactory tooth adhesion agent once the bleaching composition is sufficiently moistened, it presents a shrinkage problem that can cause undesirable deformation of thin, flexible polymer sheets. One would expect Carbopol 974 P to work better when used with less flexible sheets and/or preformed dental trays of sufficient rigidity to avoid shriveling or unwanted deformation.

EXAMPLE 4

An initially flowable dental bleaching composition suitable for use in manufacturing a substantially solid, cohesive, and non-flowable dental bleaching composition was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The resulting bleaching gel was spread over the surface of MYLAR sheets as in Example 2. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The bleaching composition of Example 4 did not adhere at all to the MYLAR sheets. This indicates that the lower molecular weight polyethylene oxide of Example 4 was even less adhesive to MYLAR sheets than the higher molecular weight polyethylene oxide of Example 2. Sheets comprising a solid layer of the bleaching composition of Example 2 could also be formed by spreading the composition on a solid surface such as glass, drying the composition, and then peeling off the dried composition.

By comparison, when the bleaching composition of Example 1 was applied to a glass surface and then dried, it adhered so strongly that it could not readily be peeled off the glass surface. Instead, it had to be forcefully chipped or pried off using a razor blade.

The dried bleaching composition of Example 4 did, however, adhere to a person's teeth when moistened, although not as well as the bleaching compositions of Examples 1–3. This indicates that the composition of Example 4 might have commercial application in a tray-like dental bleaching device to the extent that problems adhering to the barrier layer are overcome or are not an issue.

EXAMPLE 5

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The resulting bleaching composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The bleaching composition had dried sufficiently so as to form a solid, coherent layer of bleaching layer on the surface of the polymer sheets. Using a mixture of water and ethanol as the solvent allowed the bleaching composition to dry in less than time than the compositions of Examples 1–4. The inclusion of glycerin helped the bleaching composition remain more flexible and less brittle after drying. The dried bleaching composition adhered well to each of the polymer sheets. After initial drying, the coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 6

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The resulting bleaching composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The bleaching composition had dried sufficiently so as to form a solid, coherent layer of bleaching layer on the surface of the polymer sheets. The inclusion of polyethylene glycol helped the bleaching composition remain more flexible and less brittle after drying. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 7

An initially flowable dental bleaching composition suitable for use in manufacturing a substantially solid, cohesive, and non-flowable dental bleaching composition was formed by mixing together the following components:

| | |
|---|---|
| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. Using ethanol as the only solvent allowed the bleaching composition to dry in even less time than the compositions of Examples 5 and 6. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 8

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 65% |
| Kollidon VA 90 F (M.W. = 1.3 million) | 20% |
| PEG 600 | 5% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 9

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 10

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The resulting bleaching composition was spread over the surfaces of polyethylene, paraffin, and MYLAR sheets as described in Example 1. Aerosil 200 was added as a tackifying agent to promote adhesion of the wet bleaching composition to the polymer sheets. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 11

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 12

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The resulting bleaching gel was spread over the surface of MYLAR sheets as in Example 2. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The bleaching composition of Example 12 did not adhere well to the MYLAR sheets. It also shrunk somewhat after extended drying. The dried bleaching composition of Example 12 was able to adhere to a person's teeth when moistened.

EXAMPLE 13

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 14

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 15

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and shaped into tray-like dental bleaching devices suitable for placement over a person's teeth. The tray-like bleaching devices included front and rear side walls that defined a trough having an approximate U- or V-shaped cross section and were curved in the longitudinal dimension to roughly approximate the curvature of a dental arch. The tray-like dental bleaching devices adhered almost immediately when placed over a person's teeth and caused a noticeable bleaching effect within 1–3 sessions.

EXAMPLE 16

An initially flowable dental desensitizing composition suitable for use in manufacturing a substantially solid, cohesive, and non-flowable dental desensitizing composition was formed by mixing together the following components:

| | |
|---|---|
| Sodium Fluoride | 0.25% |
| Polyvinyl pyrrolidone (M.W. = 1.3 million) | 30% |
| Water | 69.75% |

The resulting desensitizing composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The desensitizing composition was spread using a screeding device. The coated sheets were heated in a forced air oven heated to a temperature of 50–70° C. for approximately 1 hour. The coated sheets were removed from the oven and inspected. The desensitizing composition had dried sufficiently so as to form a solid, coherent layer of desensitizing layer on the surface of the polymer sheets. The dried desensitizing composition adhered well to each of the polymer sheets.

The coated sheets were removed from the oven a second time, cut apart into smaller-sized pieces, and shaped into tray-like dental desensitizing devices suitable for placement over a person's teeth. The tray-like desensitizing devices included front and rear side walls that defined a trough having an approximate U- or V-shaped cross section and were curved in the longitudinal dimension to roughly approximate the curvature of a dental arch.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

EXAMPLE 17

An initially flowable dental desensitizing composition suitable for use in manufacturing a substantially solid, cohesive, and non-flowable dental desensitizing composition was formed by mixing together the following components:

| | |
|---|---|
| Sodium Citrate | 5% |
| Polyvinyl pyrrolidone (M.W. = 1.3 million) | 20% |
| Water | 75% |

The resulting desensitizing composition was manufactured into desensitizing devices according to the method described in Example 16. The dried desensitizing composition adhered well to the barrier layers comprising polymer sheets.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

EXAMPLE 18

An initially flowable dental desensitizing composition suitable for use in manufacturing a substantially solid, cohesive, and non-flowable dental desensitizing composition was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The resulting desensitizing composition was manufactured into desensitizing devices according to the method described in Example 16. The dried desensitizing composition adhered well to the barrier layers comprising polymer sheets.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

EXAMPLE 19

An initially flowable dental desensitizing composition suitable for use in manufacturing a substantially solid, cohesive, and non-flowable dental desensitizing composition was formed by mixing together the following components:

| | |
|---|---|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The resulting desensitizing composition was manufactured into desensitizing devices according to the method described in Example 16. The dried desensitizing composition adhered well to the barrier layers comprising polymer sheets.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

EXAMPLE 20

An initially flowable desensitizing bleaching composition suitable for use in manufacturing a substantially solid, cohesive, and non-flowable desensitizing bleaching composition was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The resulting desensitizing composition was manufactured into desensitizing devices according to the method described in Example 16. The dried desensitizing composition adhered well to the barrier layers comprising polymer sheets.

The tray-like desensitizing bleaching devices were tested by placing them over a person's teeth. The residual saliva present on the tooth surfaces moistened the exposed surface of the dry dental desensitizing composition and caused it to become sticky and very adhesive to teeth almost immediately. The desensitizing bleaching devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable bleaching was detected after 1–3 desensitizing sessions.

EXAMPLE 21

Any of the dental bleaching compositions or devices of Examples 1–15 is combined with any of the dental desensitizing compositions or devices of Examples 16–20 to form a kit according to the invention suitable for bleaching and desensitizing a person's teeth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit for use in bleaching and desensitizing a person's teeth, comprising:
    at least one substantially solid dental bleaching composition having a tray-like configuration and comprising at least one dental bleaching agent and at least one tooth adhesion agent having increased adhesiveness to teeth when said dental bleaching composition is moistened by saliva or water; and
    at least one substantially solid dental desensitizing composition having a tray-like configuration and comprising at least one dental desensitizing agent and at least one tooth adhesion agent having increased adhesiveness to teeth when said desensitizing composition is moistened by saliva or water,
    at least one of the dental bleaching composition or dental desensitizing composition having a rigidity so as to maintain itself in the tray-like configuration absent external support.

2. A kit as defined in claim 1, at least one of said dental bleaching composition or said desensitizing composition being initially horseshoe shaped prior to use so as to at least approximately conform to a person's dental arch with minimal longitudinal shaping.

3. A kit as defined in claim 1, at least one of said dental bleaching composition or said desensitizing composition having a longitudinal curvature that is less than the curvature of a person's dental arch prior to use so that additional longitudinal curving is required when said bleaching or desensitizing composition is placed over a person's teeth.

4. A kit as defined in claim 1, at least one of said dental bleaching composition or said desensitizing composition having a substantially straight longitudinal profile prior to use so that longitudinal curving is required when said bleaching or desensitizing composition is placed over a person's teeth.

5. A kit as defined in claim 1, at least a portion of said trough of at least one of said dental bleaching composition or said desensitizing composition having an approximate U-shaped cross section.

6. A kit as defined in claim 1, at least a portion of said trough at least one of said dental bleaching composition or said desensitizing composition having an approximate V-shaped cross section.

7. A kit as defined in claim 1, at least a portion of said trough at least one of said dental bleaching composition or said desensitizing composition having an approximate L-shaped cross section.

8. A kit as defined in claim 1, at least a portion of said trough at least one of said dental bleaching composition or said desensitizing composition having approximately a rectangular or trapezoidal cross section.

9. A kit as defined in claim 1, said dental bleaching agent comprising at least one of carbamide peroxide, metal peroxide, percarbonate, perborate, peroxy acid, peroxy acid salt, chlorite, or hypochlorite.

10. A kit as defined in claim 1, said dental bleaching agent having a concentration in a range of about 5% to about 80% by weight of said dental bleaching composition.

11. A kit as defined in claim 1, said dental bleaching agent having a concentration in a range of about 10% to about 60% by weight of said dental bleaching composition.

12. A kit as defined in claim 1, said dental bleaching agent having a concentration in a range of about 20% to about 50% by weight of said dental bleaching composition.

13. A kit as defined in claim 1, said dental desensitizing agent comprising at least one of potassium nitrate, potassium salt, citric acid, citrate, strontium chloride, sodium fluoride, or stannous fluoride.

14. A kit as defined in claim 1, said dental desensitizing agent having a concentration in a range of about 0.01% to about 50% by weight of said desensitizing composition.

15. A kit as defined in claim 1, said dental desensitizing agent having a concentration in a range of about 0.5% to about 25% by weight of said desensitizing composition.

16. A kit as defined in claim 1, said dental desensitizing agent having a concentration in a range of about 0.1% to about 10% by weight of said desensitizing composition.

17. A kit as defined in claim 1, said tooth adhesion agent in at least one of said dental bleaching composition or said dental desensitizing composition comprising polyvinyl pyrrolidone.

18. A kit as defined in claim 1, said tooth adhesion agent in at least one of said dental bleaching composition or said dental desensitizing composition comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

19. A kit as defined in claim 1, said tooth adhesion agent in at least one of said dental bleaching composition or said dental desensitizing composition having a concentration in a range of about 10% to about 90% by weight of said bleaching composition or said desensitizing composition.

20. A kit as defined in claim 1, said tooth adhesion agent in at least one of said dental bleaching composition or said dental desensitizing composition having a concentration in a range of about 20% to about 80% by weight of said bleaching composition or said desensitizing composition.

21. A kit as defined in claim 1, said tooth adhesion agent in at least one of said dental bleaching composition or said dental desensitizing composition having a concentration in a range of about 40% to about 75% by weight of said bleaching composition or said desensitizing composition.

22. A kit as defined in claim 1, wherein at least one of said dental bleaching composition or said desensitizing composition is sized and configured so as to approximately terminate at or near a person's gingival margin when said dental bleaching composition or said dental desensitizing composition is in use.

23. A kit as defined in claim 1, wherein at least one of said bleaching composition or said desensitizing composition is contained within a scaled package prior to use.

24. A kit as defined in claim 1, further comprising a barrier layer comprising a moisture-resistant material adjacent to an outer surface of at least one of said bleaching composition or said desensitizing composition that protects said bleaching or desensitizing composition from saliva or moisture when in use.

25. A kit as defined in claim 24, said barrier layer being flexible so that it will readily conform to the shape of a person's teeth when in use.

26. A kit as defined in claim 24, said barrier layer comprising at least one polyolefin.

27. A kit as defined in claim 26, said polyolefin comprising at least one of polyethylene, high density polyethylene, low density polyethylene, ultra-low density polyethylene, polypropylene, or polytetrafluoroethylene.

28. A kit as defined in claim 24, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

29. A kit for use in bleaching and desensitizing a person's teeth, comprising:
  at least one dental bleaching device that comprises:
    a first barrier layer comprising a moisture-resistant material and having a tray-like configuration; and
    a bleaching layer adjacent said first barrier layer comprising a substantially solid dental bleaching composition comprising at least one dental bleaching agent and at least one toot adhesion agent having increased adhesiveness to teeth when said bleaching layer is moistened by saliva or water; and
  at least one dental desensitizing device that comprises:
    a second barrier layer comprising a moisture-resistant material and having a tray-like configuration; and
    a desensitizing layer adjacent said second barrier layer comprising a substantially solid dental desensitizing composition comprising at least one dental desensitizing agent and at least one tooth adhesion agent having increased adhesiveness to teeth when said dental desensitizing layer is moistened by saliva or water,
      at least one of said bleaching layer or said desensitizing layer being in the shape of a dental tray and having a rigidity so as to at least partially contribute to maintaining said dental bleaching device and/or said dental desensitizing device in the tray-like configuration prior to placing said dental bleaching device and/or said dental desensitizing device over a person's teeth.

30. A kit as defined in claim 29, at least one of said first or second barrier layers being initially horseshoe shaped prior to use so as to at least approximately conform to a person's dental arch with minimal longitudinal shaping.

31. A kit as defined in claim 29, at least one of said first or second barrier layers having a longitudinal curvature that is less than the curvature of a person's dental arch prior to use so that additional longitudinal curving is required when said dental bleaching device or said dental desensitizing device is placed over a person's teeth.

32. A kit as defined in claim 29, at least one of said first or second barrier layers having a substantially straight longitudinal profile prior to use so that longitudinal curving is required when said dental bleaching composition or said dental desensitizing composition is placed over a person's teeth.

33. A kit as defined in claim 29, at least a portion of said trough of at least one of said first or second barrier layers having an approximate U-shaped cross section.

34. A kit as defined in claim 29, at least a portion of said trough at least one of said first or second barrier layers having an approximate V-shaped cross section.

35. A kit as defined in claim 29, at least a portion of said trough at least one of said first or second barrier layers having an approximate L-shaped cross section.

36. A kit as defined in claim 29, at least a portion of said trough at least one or said first or second barrier layers having an approximately rectangular or trapezoidal cross section.

37. A kit as defined in claim 29, said dental bleaching agent comprising at least one of carbamide peroxide, metal peroxide, percarbonate, perborate, peroxy acid, peroxy acid salt, chlorite, or hypochlorite.

38. A kit as defined in claim 29, said desensitizing agent comprising at least one of potassium nitrate, other potassium salts, citric acid, citrates, strontium chloride, sodium fluoride, or stannous fluoride.

39. A kit as defined in claim 29, said tooth adhesion agent in at least one or said dental bleaching composition or said dental desensitizing composition comprising polyvinyl pyrrolidone.

40. A kit as defined in claim 29, said toot adhesion agent in at least one of said dental bleaching composition or said dental desensitizing composition comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

41. A kit as defined in claim 29, wherein at least one of said first or second barrier layers is sized and configured so as to approximately terminate at or near a person's gingival margin when said dental bleaching device or said dental desensitizing device is in use.

42. A kit as defined in claim 29, wherein at least one of said dental bleaching device or said dental desensitizing device is contained within a scaled package prior to use.

43. A kit as defined in claim 29, at least one of said first or second barrier layers being flexible so that it will readily conform to the shape of a person's teeth when in use.

44. A kit as defined in claim 29, at least one of said first or second barrier layers comprising at least one polyolefin.

45. A kit as defined in claim 29, at least one of said first or second barrier layers comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

46. A method for bleaching and desensitizing a person's teeth, comprising:
- (1) placing a substantially solid dental bleaching composition having a tray-like configuration over the person's teeth for a desired period of time, said dental bleaching composition having a rigidity so as to maintain itself in the tray-like configuration absent external support, said bleaching composition comprising:
  - at least one dental bleaching agent; and
  - at least one tooth adhesion agent having increased adhesiveness to teeth when said bleaching composition is moistened by saliva or water;
- (2) removing said dental bleaching composition;
- (3) placing a substantially solid dental desensitizing composition having a tray-like configuration over the person's teeth for a desired period of time, said desensitizing composition comprising:
  - at least one dental desensitizing agent; and
  - at least one tooth adhesion agent having increased adhesiveness to teeth when said dental desensitizing composition is moistened by saliva or water; and
- (4) removing said dental desensitizing composition.

47. A method as defined in claim 46, wherein acts (1) and (2) are performed prior to acts (3) and (4).

48. A method as defined in claim 46, wherein acts (3) and (4) are performed prior to acts (1) and (2).

49. A method as defined in claim 46, at least one of said dental bleaching composition or said dental desensitizing composition further comprising a moisture-resistant barrier layer adjacent thereto.

50. A method as defined in claim 49, said barrier layer being applied to said at least one dental bleaching composition or said dental desensitizing composition immediately prior to placing said dental bleaching composition or said dental desensitizing composition over the person's teeth.

51. A method as defined in claim 49, said barrier layer being attached to said at least one dental bleaching composition or said dental desensitizing composition during manufacture of said dental bleaching composition or said dental desensitizing composition.

* * * * *

UNITED STATES PATENT AND TRADEMARK OFFICE
CERTIFICATE OF CORRECTION

PATENT NO. : 7,052,275 B2
APPLICATION NO. : 10/646443
DATED : May 30, 2006
INVENTOR(S) : Allred et al.

It is certified that error appears in the above-identified patent and that said Letters Patent is hereby corrected as shown below:

Column 7
Line 11, before "pain", remove [,]
Line 42, change "interested" to --internested--

Column 15
Line 55, remove [28]

Column 20
Line 63, change "interested" to --internested--

Column 24
Line 30, after "Glycerin", change "73%" to --2%--

Column 34
Line 10, after "trough", insert --of--
Line 14, after "trough", insert --of--
Line 18, after "trough", insert --of--
Line 43, change "0.5%" to --0.1%--
Line 46, change "0.1%" to --0.5%--

Column 35
Line 45, change "toot" to --tooth--

UNITED STATES PATENT AND TRADEMARK OFFICE
CERTIFICATE OF CORRECTION

PATENT NO. : 7,052,275 B2
APPLICATION NO. : 10/646443
DATED : May 30, 2006
INVENTOR(S) : Allred et al.

It is certified that error appears in the above-identified patent and that said Letters Patent is hereby corrected as shown below:

Column 36
Line 19, after "trough", insert --of--
Line 22, after "trough", insert --of--
Line 25, after "trough", insert --of--
Line 41, change "toot" to --tooth--
Line 57, change "scaled" to --sealed--

Signed and Sealed this

Twenty-first Day of November, 2006

JON W. DUDAS
*Director of the United States Patent and Trademark Office*